United States Patent
Nishii et al.

[11] Patent Number: 5,756,738
[45] Date of Patent: May 26, 1998

[54] PROCESS FOR PRODUCING 1-SUBSTITUTED TETRAHYDROQUINAZOLINES

[75] Inventors: Shinji Nishii; Masashi Komatsu, both of Osaka; Sachiko Takeuchi, Nara, all of Japan

[73] Assignee: Sumitomo Chemical Company, Limited, Osaka, Japan

[21] Appl. No.: 747,822

[22] Filed: Nov. 13, 1996

[30] Foreign Application Priority Data

Nov. 14, 1995 [JP] Japan .................. 7-295435

[51] Int. Cl.$^6$ .............. C07D 239/72; C07D 401/00; C07D 413/00; C07D 419/00
[52] U.S. Cl. ............................ 544/283; 544/284
[58] Field of Search ...................... 544/283, 284

[56] References Cited

FOREIGN PATENT DOCUMENTS 0456835A  11/1991  European Pat. Off.
1-25767   5/1989  Japan.

OTHER PUBLICATIONS

Patent Abstracts of Japan, vol. 13, No. 205 (C–595), 15 May 1989 & JP 01 025767 A (Fujisawa Pharmaceutical Co., Ltd.), 27 Jan. 1989.
Süsse M. & Johne S., Monatshefte Für Chemie/Chemical Monthly, vol. 118, No. 1, 1987, pp. 71–79, XP000650958.
Billon F. et al., "Aldose reductase inhibition by 2,4–oxo and thioxo derivatives of 1,2,3,4–tetrahydroquinazoline" European Journal of Med. Chem., vol. 25, No. 2, 1990, pp. 121–126, XP000650960.
Patent Abstracts of Japan, vol. 16, No. 13 (C–901), 14 Jan. 1992 & JP 03 232885 A (Fujisawa Pharmaceutical Co., Ltd.), 16 Oct. 1991.

El–Barbary A.A. et al., Liebigs Annalen Der Chemie, vol. 7, 1995, pp. 1371–1375, XP000651048, "Synthesis and antiviral evaluation of quinazoline, thieno–[2,3–d]pyrimidine, and lumazine analogues of 3'–fluoro–3'–deoxythymidine (FLT)".

*Primary Examiner*—Mukund J. Shah
*Assistant Examiner*—Bruce Kifle
*Attorney, Agent, or Firm*—Sughrue, Mion, Zinn, Macpeak & Seas, PLLC

[57] ABSTRACT

A process for producing 1-substituted tetrahydroquinazolines represented by the formula (III):

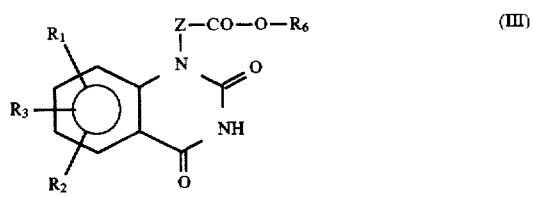

as defined herein which comprises reacting tetrahydroquinazolines represented by the formula (I):

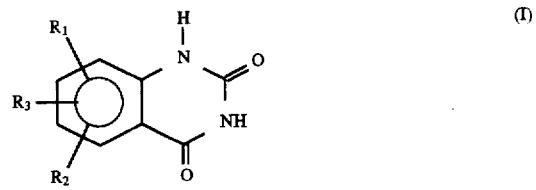

with hexamethyldisilazane; and reacting the resultant product with a chloroalkanoate represented by the formula (II):

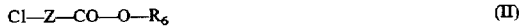

in the presence of an iodide of an alkaline metal, followed by desilylation.

13 Claims, No Drawings

PROCESS FOR PRODUCING 1-SUBSTITUTED TETRAHYDROQUINAZOLINES

BACKGROUND OF THE INVENTION

1. Field of the Invention

The present invention relates to a process for producing 1-substituted tetrahydroquinazolines of formula (III). More particularly, it relates to a process for producing 1-substituted tetrahydroquinazolines of formula (III) which comprises reacting tetrahydroquinazolines of formula (I) with hexamethyldisilazane; reacting the resultant product with a chloroalkanoate of formula (II) in the presence of an iodide of an alkaline metal; followed by desilylation.

2. Description of the Related Art

1-Substituted tetrahydroquinazolines of formula (III) are compounds known as intermediates for antiphlogistics, and remedies for diabetic complications; it is also known that 1-substituted tetrahydroquinazolines of formula (III) are produced by reacting tetrahydroquinazolines of formula (I) with hexamethyldisilazane; reacting the resultant product with a bromoalkanoate; followed by desilylation (see, e.g., JP-A-64-25767).

However, this process is disadvantageous because expensive bromoalkanoate is used.

On the other hand, a process for producing 1-substituted tetrahydroquinazolines of formula (III) in which an inexpensive chloroalkanoate of formula (II) is used in place of the bromoalkanoate is also disadvantageous in that the yield is drastically lowered.

The present inventors have intensively studied the process for producing 1-substituted tetrahydroquinazolines of formula (III) so as to solve the above-mentioned drawbacks. As a result, it has been found, according to the present invention, that the desired product can be produced with high yield in an industrially advantageous manner, when the chloroalkanoate of formula (II) is used in place of the bromoalkanoate and the reaction is conducted in the presence of an iodide of an alkaline metal.

SUMMARY OF THE INVENTION

Accordingly, the present invention provides a process for producing 1-substituted tetrahydroquinazolines represented by the formula (III):

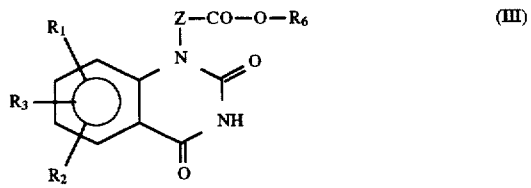

wherein

Z represents a methylene group which is optionally substituted by an alkyl group;

$R_6$ represents an alkyl group or an aralkyl group;

$R_1$ and $R_2$ independently represent a hydrogen atom, a halogen atom, a nitro group, an azido group, an alkyl group which is optionally substituted with one or more halogen atoms, an alkenyl group which is optionally substituted with one or more halogen atoms, an aralkyl group which is optionally substituted with one or more halogen atoms, an alkoxy group which is optionally substituted with one or more halogen atoms, an alkoxy-carbonyl group which is optionally substituted with one or more halogen atoms, an acyloxy group, or an amino group represented by $XNR_4R_5$ in which X represents a direct bond, an alkylene group or a carbonyl group, or N, $R_4$ and $R_5$ may form together a five- or six-membered heterocyclic ring which optionally contains another hetero atom which may be substituted or when X is a direct bond or an alkylene group, $R_4$ and $R_5$ independently represent an alkyl group or when X is a carbonyl group, $R_4$ and $R_5$ independently represent an acyloxy alkyl group; and $R_3$ represents a hydrogen atom, a halogen atom, a nitro group, an azido group, alkyl group which is optionally substituted with one or more halogen atoms, an alkenyl group which is optionally substituted with one or more halogen atoms, an aralkyl group which is optionally substituted with one or more halogen atoms, an alkoxy group which is optionally substituted with one or more halogen atoms, or an alkoxycarbonyl group which is optionally substituted with one or more halogen atoms; which comprises reacting a tetrahydroquinazoline represented by the formula (I):

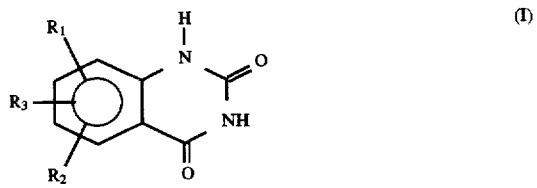

wherein $R_1$, $R_2$ and $R_3$ are as defined above with hexamethyldisilazane; and reacting the resultant product with a chloroalkanoate represented by the formula (II):

wherein Z and $R_6$ are as defined above, in the presence of an iodide of an alkali metal, followed by desilylation.

DETAILED DESCRIPTION OF THE PREFERRED EMBODIMENTS

Hereinafter, the present invention will be described in detail.

The substituents $R_1$ and $R_2$ in the tetrahydroquinazolines of formula (I), the starting material of the present invention, independently represent a hydrogen atom, a halogen atom, a nitro group, an azido group, an alkyl group which is optionally substituted with one or more halogen atoms, an alkenyl group which is optionally substituted with one or more halogen atoms, an aralkyl group which is optionally substituted with one or more halogen atoms, an alkoxy group which is optionally substituted with one or more halogen atoms, an alkoxycarbonyl group which is optionally substituted with one or more halogen atoms, an acyloxy group, or an amino group represented by $XNR_4R_5$ in which X represents a direct bond, an alkylene group or a carbonyl group, and N, $R_4$ and $R_5$ may form together a five- or six-membered heterocyclic ring which optionally contains another hetero atom which may be substituted or when X is a direct bond or an alkylene group, $R_4$ and $R_5$ independently represent an alkyl group or when X is a carbonyl group, $R_4$ and $R_5$ independently represent an acyloxy alkyl group.

Examples of the halogen atom include chlorine, bromine and fluorine.

Examples of the alkyl group which is optionally substituted with the halogen atom include lower alkyl groups such as methyl, ethyl, propyl, i-propyl, butyl, i-butyl, t-butyl, pentyl, i-pentyl and hexyl; monohalo lower alkyl groups such as chloromethyl, bromomethyl and chloropropyl; and dihalo lower alkyl groups such as 1,2-dichloroethyl, 1,2-dibromoethyl and 2,2-dichloroethyl; and trihalo lower alkyl groups such as trifluoromethyl. (By "lower", as used in this specification, is meant "one to six carbon atoms".)

Examples of the alkenyl group which is optionally substituted with the halogen atom include lower alkenyl groups such as 1-propenyl, 2-propenyl, 1-butenyl, 2-butenyl, 3-butenyl, 1-pentenyl, 2-pentenyl, 3-pentenyl and 4-pentenyl; monohalo lower alkenyl groups such as 3-chloro-1-propenyl and 3-chloro-1-butenyl; and dihalo lower alkenyl groups such as 3,4-dichloro-1-butenyl; and trihalo lower alkenyl groups such as 3,4,5-trichloro-1-pentenyl.

Examples of the aralkyl group which is optionally substituted with the halogen atom include benzyl, phenylethyl, 4-chlorobenzyl, 2-4-dichlorobenzyl and 2,4-dibromobenzyl.

Examples of the alkoxy group which is optionally substituted with the halogen atom include lower alkoxy groups such as methoxy, ethoxy, propoxy, i-propoxy, butoxy, i-butoxy, t-butoxy, pentyloxy, i-pentyloxy and hexyloxy; halogenated lower alkoxy groups such as chloromethoxy, bromomethoxy, 1-chloroethoxy, 2-chloroethoxy, 1-chloropropoxy, 2-chloropropoxy, 3-chloropropoxy, dichloromethoxy, dibromomethoxy, 1,2-dichloroethoxy, 2,2-dichloroethoxy, and trifluoromethoxy.

Examples of the alkoxycarbonyl group which is optionally substituted with the halogen atom include carbonyl groups substituted with an alkoxy group such as those exemplified above.

Examples of the acyloxy group include lower alkylcarbonyloxy groups such as acetoxy, propionyloxy, butylyloxy, i-butylyloxy, valeryloxy, i-valeryloxy and pivaloyloxy; and arylcarbonyloxy such as benzyloxy.

Examples of the alkylene group represented by X in the amino group $XNR_4R_5$ include lower alkylene groups such as methylene, dimethylene, trimethylene and tetramethylene.

Examples of $R_4$ and $R_5$ as the lower alkyl group in the amino group $XNR_4R_5$ include the same lower alkyl group as that exemplified above. In this case, specific examples of the amino group of $XNR_4R_5$ include dimethylamino, diethylamino, dipropylamino and dibutylamino.

Specific examples of the amino group of $XNR_4R_5$, in case that N, $R_4$ and $R_5$ form together to a five- or six-membered heterocyclic ring which optionally have another hetero atom, include pyrrolyl, 2H, 4H-pyrrolyl, pyrrolidino, pyrazolyl, piperidino, piperazinyl, morpholino and imidazolyl.

When the other hetero atom in the heterocyclic ring is a nitrogen atom, it may be substituted. Examples of the substituent include alkyl groups such as those exemplified above, aralkyl groups such as those exemplified above, aralkyl groups which are optionally substituted by an alkoxy group and a phenylcarbonyl group which is optionally substituted by an alkoxy group.

Examples of the tetrahydroquinazolines (I) include 2,4-dioxo-1,2,3,4-tetrahydroquinazoline, 5-chloro-2,4-dioxo-1,2,3,4-tetrahydroquinazoline, 6-chloro-2,4-dioxo-1,2,3,4-tetrahydroquinazoline, 7-chloro-2,4-dioxo-1,2,3,4-tetrahydroquinazoline, 8-chloro-2,4-dioxo-1,2,3,4-tetrahydroquinazoline, 5-bromo-2,4-dioxo-1,2,3,4-tetrahydroquinazoline, 6-bromo-2,4-dioxo-1,2,3,4-tetrahydroquinazoline, 7-bromo-2,4-dioxo-1,2,3,4-tetrahydroquinazoline, 8-bromo-2,4-dioxo-1,2,3,4-tetrahydroquinazoline, 5-fluoro-2,4-dioxo-1,2,3,4-tetrahydroquinazoline, 6-fluoro-2,4-dioxo-1,2,3,4-tetrahydroquinazoline, 7-fluoro-2,4-dioxo-1,2,3,4-tetrahydroquinazoline, 8-fluoro-2,4-dioxo-1,2,3,4-tetrahydroquinazoline, 5,6-dichloro-2,4-dioxo-1,2,3,4-tetrahydroquinazoline, 5,7-dichloro-2,4-dioxo-1,2,3,4-tetrahydroquinazoline, 5,8-dichloro-2,4-dioxo-1,2,3,4-tetrahydroquinazoline, 6,7-dichloro-2,4-dioxo-1,2,3,4-tetrahydroquinazoline, 6,8-dichloro-2,4-dioxo-1,2,3,4-tetrahydroquinazoline, 7,8-dichloro-2,4-dioxo-1,2,3,4-tetrahydroquinazoline, 5,6-dibromo-2,4-dioxo-1,2,3,4-tetrahydroquinazoline, 5,7-dibromo-2,4-dioxo-1,2,3,4-tetrahydroquinazoline, 5,8-dibromo-2,4-dioxo-1,2,3,4-tetrahydroquinazoline, 6,7-dibromo-2,4-dioxo-1,2,3,4-tetrahydroquinazoline, 6,8-dibromo-2,4-dioxo-1,2,3,4-tetrahydroquinazoline, 7,8-dibromo-2,4-dioxo-1,2,3,4-tetrahydroquinazoline, 5,6-difluoro-2,4-dioxo-1,2,3,4-tetrahydroquinazoline, 5,7-difluoro-2,4-dioxo-1,2,3,4-tetrahydroquinazoline, 5,8-difluoro-2,4-dioxo-1,2,3,4-tetrahydroquinazoline, 6,7-difluoro-2,4-dioxo-1,2,3,4-tetrahydroquinazoline, 7,8-difluoro-2,4-dioxo-1,2,3,4-tetrahydroquinazoline, 5-bromo-6-chloro-2,4-dioxo-1,2,3,4-tetrahydroquinazoline, 5-bromo-7-chloro-2,4-dioxo-1,2,3,4-tetrahydroquinazoline, 5-bromo-8-chloro-2,4-dioxo-1,2,3,4-tetrahydroquinazoline, 6-bromo-5-chloro-2,4-dioxo-1,2,3,4-tetrahydroquinazoline, 6-bromo-7-chloro-2,4-dioxo-1,2,3,4-tetrahydroquinazoline, 6-bromo-8-chloro-2,4-dioxo-1,2,3,4-tetrahydroquinazoline, 7-bromo-5-chloro-2,4-dioxo-1,2,3,4-tetrahydroquinazoline, 7-bromo-6-chloro-2,4-dioxo-1,2,3,4-tetrahydroquinazoline, 7-bromo-8-chloro-2,4-dioxo-1,2,3,4-tetrahydroquinazoline, 8-bromo-5-chloro-2,4-dioxo-1,2,3,4-tetrahydroquinazoline, 8-bromo-6-chloro-2,4-dioxo-1,2,3,4-tetrahydroquinazoline, 8-bromo-7-chloro-2,4-dioxo-1,2,3,4-tetrahydroquinazoline, 5,6,7-trichloro-2,4-dioxo-1,2,3,4-tetrahydroquinazoline, 5,6,8-trichloro-2,4-dioxo-1,2,3,4-tetrahydroquinazoline, 5,7,8-trichloro-2,4-dioxo-1,2,3,4-tetrahydroquinazoline, 6,7,8-trichloro-2,4-dioxo-1,2,3,4-tetrahydroquinazoline, 5,6,7-tribromo-2,4-dioxo-1,2,3,4-tetrahydroquinazoline, 5,6,8-tribromo-2,4-dioxo-1,2,3,4-tetrahydroquinazoline, 5,7,8-tribromo-2,4-dioxo-1,2,3,4-tetrahydroquinazoline, 6,7,8-tribromo-2,4-dioxo-1,2,3,4-tetrahydroquinazoline, 5,6,7-trifluoro-2,4-dioxo-1,2,3,4-tetrahydroquinazoline, 5,6,8-trifluoro-2,4-dioxo-1,2,3,4-tetrahydroquinazoline, 5,7,8-trifluoro-2,4-dioxo-1,2,3,4-tetrahydroquinazoline, 6,7,8-trifluoro-2,4-dioxo-1,2,3,4-tetrahydroquinazoline, 5-nitro-2,4-dioxo-1,2,3,4-tetrahydroquinazoline, 6-nitro-2,4-dioxo-1,2,3,4-tetrahydroquinazoline, 7-nitro-2,4-dioxo-1,2,3,4-tetrahydroquinazoline, 8-nitro-2,4-dioxo-1,2,3,4-tetrahydroquinazoline, 5-azido-2,4-dioxo-1,2,3,4-tetrahydroquinazoline, 6-azido-2,4-dioxo-1,2,3,4-tetrahydroquinazoline, 7-azido-2,4-dioxo-1,2,3,4-tetrahydroquinazoline, 8-azido-2,4-dioxo-1,2,3,4-tetrahydroquinazoline, 5-carboxy-2,4-dioxo-1,2,3,4-tetrahydroquinazoline, 6-carboxy-2,4-dioxo-1,2,3,4-tetrahydroquinazoline, 7-carboxy-2,4-dioxo-1,2,3,4-tetrahydroquinazoline, 8-carboxy-2,4-dioxo-1,2,3,4-tetrahydroquinazoline, 5-methyl-2,4-dioxo-1,2,3,4-tetrahydroquinazoline, 6-methyl-2,4-dioxo-1,2,3,4-tetrahydroquinazoline, 7-methyl-2,4-dioxo-1,2,3,4-tetrahydroquinazoline, 8-methyl-2,4-dioxo-1,2,3,4-tetrahydroquinazoline, 5-ethyl-2,4-dioxo-1,2,3,4-tetrahydroquinazoline, 6-ethyl-2,4-dioxo-1,2,3,4-tetrahydroquinazoline, 7-ethyl-2,4-dioxo-1,2,3,4- tetrahydroquinazoline, 8-ethyl-2,4-dioxo-1,2,3,4-tetrahydroquinazoline, 5-propyl-2,4-dioxo-1,2,3,4-tetrahydroquinazoline, 6-propyl-2,4-dioxo-1,2,3,4-tetrahydroquinazoline, 7-propyl-2,4-dioxo-1,2,3,4-tetrahydroquinazoline, 8-propyl-2,4-dioxo-1,2,3,4-tetrahydroquinazoline, 5-i-propyl-2,4-dioxo-1,2,3,4-tetrahydroquinazoline, 6-i-propyl-2,4-dioxo-1,2,3,4-tetrahydroquinazoline, 7-i-propyl-2,4-dioxo-1,2,3,4-tetrahydroquinazoline, 8-i-propyl-2,4-dioxo-1,2,3,4-tetrahydroquinazoline, 5-chloromethyl-2,4-dioxo-1,2,3,4-tetrahydroquinazoline, 6-chloromethyl-2,4-dioxo-1,2,3,4-tetrahydroquinazoline, 7-chloromethyl-2,4-dioxo-1,2,3,4-tetrahydroquinazoline, 8-chloromethyl-2,4-dioxo-1,2,3,4-tetrahydroquinazoline, 5-bromomethyl-2,4-dioxo-1,2,3,4-tetrahydroquinazoline, 6-bromomethyl-2,4-dioxo-1,2,3,4-tetrahydroquinazoline, 7-bromomethyl-2,4-dioxo-1,2,3,4-tetrahydroquinazoline, 8-bromomethyl-2,4-dioxo-1,2,3,4-tetrahydroquinazoline, 5-(1-chloroethyl)-2,4-dioxo-1,2,3,4-tetrahydroquinazoline, 6-(1-chloroethyl)-2,4-dioxo-1,2,3,4-tetrahydroquinazoline, 7-(1-chloroethyl)2,4-dioxo-1,2,3,4-tetrahydroquinazoline, 8-(1-chloroethyl)-2,4-dioxo-1,2,3,4-tetrahydroquinazoline, 5-(2-chloroethyl)-2,4-dioxo-1,2,3,4-tetrahydroquinazoline, 6-(2-chloroethyl)-2,4-dioxo-1,2,3,4-tetrahydroquinazoline, 7-(2-chloroethyl)-2,4-dioxo-1,2,3,4-tetrahydroquinazoline, 8-(2-chloroethyl)-2,4-dioxo-1,2,3,4-tetrahydroquinazoline, 5-dichloromethyl-2,4-dioxo-1,2,3,4-tetrahydroquinazoline, 6-dichloromethyl-2,4-dioxo-1,2,3,4-tetrahydroquinazoline, 7-dichloromethyl-2,4-dioxo-1,2,3,4-tetrahydroquinazoline, 8-dichloromethyl-2,4-dioxo-1,2,3,4-tetrahydroquinazoline, 5-(1,2-dichloroethyl)-2,4-dioxo-1,2,3,4-tetrahydroquinazoline, 6-(1,2-dichloroethyl)-2,4-dioxo-1,2,3,4-tetrahydroquinazoline, 7-(1,2-dichloroethyl)-2,4-dioxo-1,2,3,4-tetrahydroquinazoline, 8-(1,2-dichloroethyl)-2,4-dioxo-1,2,3,4-tetrahydroquinazoline, 5-(2,2-dichloroethyl)-2,4-dioxo-1,2,3,4-tetrahydroquinazoline, 6-(2,2-dichloroethyl)-2,4-dioxo-1,2,3,4-tetrahydroquinazoline, 7-(2,2-dichloroethyl)-2,4-dioxo-1,2,3,4-tetrahydroquinazoline, 8-(2,2-dichloroethyl)-2,4-dioxo-1,2,3,4-tetrahydroquinazoline, 5-(2,2-dichloroethyl)-2,4-dioxo-1,2,3,4-tetrahydroquinazoline, 5-ethenyl-2,4-dioxo-1,2,3,4-tetrahydroquinazoline, 6-ethenyl-2,4-dioxo-1,2,3,4-tetrahydroquinazoline, 7-ethenyl-2,4-dioxo-1,2,3,4-tetrahydroquinazoline, 8-ethenyl-2,4-dioxo-1,2,3,4-tetrahydroquinazoline, 5-(1-propenyl)-2,4-dioxo-1,2,3,4-tetrahydroquinazoline, 6-(1-propenyl)-2,4-dioxo-1,2,3,4-tetrahydroquinazoline, 7-(1-propenyl)-2,4-dioxo-1,2,3,4-tetrahydroquinazoline, 8-(2-propenyl)-2,4-dioxo-1,2,3,4-tetrahydroquinazoline, 5-(2-propenyl)-2,4-dioxo-1,2,3,4-tetrahydroquinazoline, 6-(2-propenyl)-2,4-dioxo-1,2,3,4-tetrahydroquinazoline, 7-(2-propenyl)-2,4-dioxo-1,2,3,4-tetrahydroquinazoline, 8-(2-propenyl)-2,4-dioxo-1,2,3,4-tetrahydroquinazoline, 5-(1-butenyl)-2,4-dioxo-1,2,3,4-tetrahydroquinazoline, 6-(1-butenyl)-2,4-dioxo-1,2,3,4-tetrahydroquinazoline, 7-(1-butenyl)-2,4-dioxo-1,2,3,4-tetrahydroquinazoline, 8-(1-butenyl)-2,4-dioxo-1,2,3,4-tetrahydroquinazoline, 5-(1-pentenyl)-2,4-dioxo-1,2,3,4-tetrahydroquinazoline, 6-(1-pentenyl)-2,4-dioxo-1,2,3,4-tetrahydroquinazoline, 7-(1-pentenyl)-2,4-dioxo-1,2,3,4-tetrahydroquinazoline, 8-(1-pentenyl)-2,4-dioxo-1,2,3,4-tetrahydroquinazoline, 5-(3-chloro-1-propenyl)-2,4-dioxo-1,2,3,4-tetrahydroquinazoline, 6-(3-chloro-1-propenyl)-2,4-dioxo-1,2,3,4-tetrahydroquinazoline, 7-(3-chloro-1-propenyl)-2,4-dioxo-1,2,3,4-tetrahydroquinazoline, 8-(3-chloro-1-propenyl)-2,4-dioxo-1,2,3,4-tetrahydroquinazoline, 5-(3,4-dichloro-1-butenyl)-2,4-dioxo-1,2,3,4-tetrahydroquinazoline, 6-(3,4-dichloro-1-butenyl)-2,4-dioxo-1,2,3,4-tetrahydroquinazoline, 7-(3,4-dichloro-1-butenyl)-2,4-dioxo-1,2,3,4-tetrahydroquinazoline, 8-(3,4-dichloro-1-butenyl)-2,4-dioxo-1,2,3,4-tetrahydroquinazoline, 5-methoxy-2,4-dioxo-1,2,3,4-tetrahydroquinazoline, 6-methoxy-2,4-dioxo-1,2,3,4-tetrahydroquinazoline, 7-methoxy-2,4-dioxo-1,2,3,4-tetrahydroquinazoline, 8-methoxy-2,4-dioxo-1,2,3,4-tetrahydroquinazoline, 5-ethoxy-2,4-dioxo-1,2,3,4-tetrahydroquinazoline, 6-ethoxy-2,4-dioxo-1,2,3,4-tetrahydroquinazoline, 7-ethoxy-2,4-dioxo-1,2,3,4-tetrahydroquinazoline, 8-ethoxy-2,4-dioxo-1,2,3,4-tetrahydroquinazoline, 5-propoxy-2,4-dioxo-1,2,3,4-tetrahydroquinazoline, 6-propoxy-2,4-dioxo-1,2,3,4-tetrahydroquinazoline, 7-propoxy-2,4-dioxo-1,2,3,4-tetrahydroquinazoline, 8-propoxy-2,4-dioxo-1,2,3,4-tetrahydroquinazoline, 5-i-propoxy-2,4-dioxo-1,2,3,4-tetrahydroquinazoline, 6-i-propoxy-2,4-dioxo-1,2,3,4-tetrahydroquinazoline, 7-i-propoxy-2,4-dioxo-1,2,3,4-tetrahydroquinazoline, 8-i-propoxy-2,4-dioxo-1,2,3,4-tetrahydroquinazoline, 5-t-butoxy-2,4-dioxo-1,2,3,4-tetrahydroquinazoline, 6-t-butoxy-2,4-dioxo-1,2,3,4-tetrahydroquinazoline, 7-t-butoxy-2,4-dioxo-1,2,3,4-tetrahydroquinazoline, 8-t-butoxy-2,4-dioxo-1,2,3,4-tetrahydroquinazoline, 5-chloromethoxy-2,4-dioxo-1,2,3,4-tetrahydroquinazoline, 6-chloromethoxy-2,4-dioxo-1,2,3,4-tetrahydroquinazoline, 7-chloromethoxy-2,4-dioxo-1,2,3,4-tetrahydroquinazoline, 8-chloromethoxy-2,4-dioxo-1,2,3,4-tetrahydroquinazoline, 5-bromomethoxy-2,4-dioxo-1,2,3,4-tetrahydroquinazoline, 6-bromomethoxy-2,4-dioxo-1,2,3,4-tetrahydroquinazoline, 7-bromomethoxy-2,4-dioxo-1,2,3,4-tetrahydroquinazoline, 8-bromomethoxy-2,4-dioxo-1,2,3,4-tetrahydroquinazoline, 5-(2-chloroethoxy)-2,4-dioxo-1,2,3,4-tetrahydroquinazoline, 6-(2-chloroethoxy)-2,4-dioxo-1,2,3,4-tetrahydroquinazoline, 7-(2-chloroethoxy)-2,4-dioxo-1,2,3,4-tetrahydroquinazoline, 8-(2-chloroethoxy)-2,4-dioxo-1,2,3,4-tetrahydroquinazoline, 5-(1-chloropropoxy)-2,4-dioxo-1,2,3,4-tetrahydroquinazoline, 6-(1-chloropropoxy)-2,4-dioxo-1,2,3,4-tetrahydroquinazoline, 7-(1-chloropropoxy)-2,4-dioxo-1,2,3,4-tetrahydroquinazoline, 8-(1-chloropropoxy)-2,4-dioxo-1,2,3,4-tetrahydroquinazoline, 5-(2-chloropropoxy)-2,4-dioxo-1,2,3,4-tetrahydroquinazoline, 6-(2-chloropropoxy)-2,4-dioxo-1,2,3,4-tetrahydroquinazoline, 7-(2-chloropropoxy)-2,4-dioxo-1,2,3,4-tetrahydroquinazoline, 8-(2-chloropropoxy)-2,4-dioxo-1,2,3,4-tetrahydroquinazoline, 5-(3-chloropropoxy)-2,4-dioxo-1,2,3,4-tetrahydroquinazoline, 6-(3-chloropropoxy)-2,4-dioxo-1,2,3,4-tetrahydroquinazoline, 7-(3-chloropropoxy)-2,4-dioxo-1,2,3,4-tetrahydroquinazoline, 8-(3-chloropropoxy)-2,4-dioxo-1,2,3,4-tetrahydroquinazoline, 5-dichloromethoxy-2,4-dioxo-1,2,3,4-tetrahydroquinazoline, 6-dichloromethoxy-2,4-dioxo-1,2,3,4-tetrahydroquinazoline, 7-dichloromethoxy-2,4-dioxo-1,2,3,4-tetrahydroquinazoline, 8-dichloromethoxy-2,4-dioxo-1,2,3,4-tetrahydroquinazoline, 5-dibromomethoxy-2,4-dioxo-1,2,3,4-tetrahydroquinazoline, 6-dibromomethoxy-2,4-dioxo-1,2,3,4-tetrahydroquinazoline, 7-dibromomethoxy-2,4-dioxo-1,2,3,4-tetrahydroquinazoline, 8-dibromomethoxy-2,4-dioxo-1,2,3,4-tetrahydroquinazoline, 5-trifluoromethoxy-2,4-dioxo-1,2,3,4-tetrahydroquinazoline, 6-trifluoromethoxy-2,4-dioxo-1,2,3,4-tetrahydroquinazoline, 7-trifluoromethoxy-2,4-dioxo-1,2,3,4-tetrahydroquinazoline, 8-trifluoromethoxy-2,4-dioxo-1,2,3,4-tetrahydroquinazoline, 5-chloromethoxycarbonyl-2,4-dioxo-1,2,3,4-tetrahydroquinazoline, 6-chloromethoxycarbonyl-2,4-dioxo-1,2,3,4-tetrahydroquinazoline, 7-chloromethoxycarbonyl-2,4-dioxo-1,2,3,4-tetrahydroquinazoline, 8-chloromethoxycarbonyl-2,4-dioxo-1,2,3,4-tetrahydroquinazoline, 5-bromomethyoxycarbonyl-2,4-dioxo-1,2,3,4-tetrahydroquinazoline, 6-bromomethyoxycarbonyl-2,4-dioxo-1,2,3,4-tetrahydroquinazoline, 7-bromomethyoxycarbonyl-2,4-dioxo-1,2,3,4-tetrahydroquinazoline, 8-bromomethyoxycarbonyl-2,4-dioxo-1,2,3,4-tetrahydroquinazoline, 5-(1-chloroethoxycarbonyl)-2,4-dioxo-1,2,3,4-tetrahydroquinazoline, 6-(1-chloroethoxycarbonyl)-2,4-dioxo-1,2,3,4-tetrahydroquinazoline, 7-(1-chloroethoxycarbonyl)-2,4-dioxo-1,2,3,4-tetrahydroquinazoline, 8-(1-chloroethoxycarbonyl)-2,4-dioxo-1,2,3,4-tetrahydroquinazoline, 5-(2-chloroethoxycarbonyl)-2,4-dioxo-1,2,3,4-tetrahydroquinazoline, 6-(2-chloroethoxycarbonyl)-2,4-dioxo-1,2,3,4-tetrahydroquinazoline, 7-chloroethoxycarbonyl)-2,4-dioxo-1,2,3,4-tetrahydroquinazoline, 8-(2-chloroethoxycarbonyl)-2,4-dioxo-1,2,3,4-tetrahydroquinazoline, 5-(1-chloropropoxycarbonyl)-2,4-dioxo-1,2,3,4-tetrahydroquinazoline, 6-(1-chloropropoxycarbonyl)-2,4-dioxo-1,2,3,4-tetrahydroquinazoline, 7-(1-chloropropoxycarbonyl)-2,4-dioxo-1,2,3,4-tetrahydroquinazoline, 8-(1-chloropropoxycarbonyl)-2,4-dioxo-1,2,3,4-tetrahydroquinazoline, 5-dichloromethoxycarbonyl-2,4-dioxo-1,2,3,4-tetrahydroquinazoline, 6-dichloromethoxycarbonyl-2,4-dioxo-1,2,3,4-tetrahydroquinazoline, 7-dichloromethoxycarbonyl-2,4-dioxo-1,2,3,4-tetrahydroquinazoline, 8-dichloromethoxycarbonyl-2,4-dioxo-1,2,3,4-tetrahydroquinazoline, 5-dibromomethoxycarbonyl-2,4-dioxo-1,2,3,4-tetrahydroquinazoline, 6-dibromomethoxycarbonyl-2,4-dioxo-1,2,3,4-tetrahydroquinazoline, 7-dibromomethoxycarbonyl-2,4-dioxo-1,2,3,4-tetrahydroquinazoline, 8-dibromomethoxycarbonyl-2,4-dioxo-1,2,3,4-tetrahydroquinazoline, 5-(1,2-dichloroethoxycarbonyl)-2,4-dioxo-1,2,3,4-tetrahydroquinazoline, 6-(1,2-dichloroethoxycarbonyl)-2,4-dioxo-1,2,3,4-tetrahydroquinazoline, 7-(1,2-dichloroethoxycarbonyl)-2,4-dioxo-1,2,3,4-tetrahydroquinazoline, 8-(1,2-dichloroethoxycarbonyl)-2,4-dioxo-1,2,3,4-tetrahydroquinazoline, 5-(2,2-dichloroethoxycarbonyl)-2,4-dioxo-1,2,3,4-tetrahydroquinazoline, 6-(2,2-dichloroethoxycarbonyl)-2,4-dioxo-1, 2, 3, 4-tetrahydroquinazoline, 7-(2,2-dichloroethoxycarbonyl)-2,4-dioxo-1,2,3,4-tetrahydroquinazoline, 8-(2,2-dichloroethoxycarbonyl)-2,4-dioxo-1,2,3,4-tetrahydroquinazoline, 5-trifluoromethoxycarbonyl -2,4-dioxo-1,2,3,4-tetrahydroquinazoline, 6-trifluoromethoxycarbonyl-2,4-dioxo-1,2,3,4-tetrahydroquinazoline, 7-trifluoromethoxycarbonyl-2,4-dioxo-1,2,3,4-tetrahydroquinazoline, 8-trifluoromethoxycarbonyl-2,4-dioxo-1,2,3,4-tetrahydroquinazoline, 7,8-dimethyl-2,4-dioxo-1,2,3,4-tetrahydroquinazoline, 7,8-diethyl-2,4dioxo-1,2,3,4-tetrahydroquinazoline, 6-benzyl-2,4-dioxo-1,2,3,4-tetrahydrocuinazoline, 6-(2-phenylethyl)-2,4-dioxo-1,2,3,4-tetrahydroquinazoline, 6-(4-chlorobenzyl)-2,4-dioxo-1,2,3,4-tetrahydroquinazoline, 6-(2,4-dichlorobenzyl)-2,4-dioxo-1,2,3,4-tetrahydroquinazoline, 6-(2,4-dibromobenzyl)-2,4-dioxo-1,2,3,4-tetrahydroquinazoline, 5,6-dimethoxy-2,4-dioxo-1,2,3,4-tetrahydroquinazoline, 6,8-dimethoxy-2,4-dioxo-1,2,3,4-tetrahydroquinazoline, 5,8-dipropoxy-2,4-dioxo-1,2,3,4-tetrahydroquinazoline, 6-(N,N-dimethylamino)-2,4-dioxo-1,2,3,4-tetrahydroquinazoline, 6-(N,N-diethylamino)-2,4-dioxo-1,2,3,4-tetrahydroquinazoline, 6-(N,N-dimethylamino)-2,4-dioxo-1,2,3,4-tetrahydroquinazoline, 6-(N,N-dibutylamino)-2,4-dioxo-1,2,3,4-tetrahydroquinazoline, 6-(1-pyrrolyl)-2,4-dioxo-1,2,3,4-tetrahydroquinazoline, 6-(1-imidazolyl)-2,4-dioxo-1,2,3,4-tetrahydroquinazoline, 6-(1-pyrazolyl)-2,4-dioxo-1,2,3,4-tetrahydroquinazoline, 6-(2H,4H-pyrrolyl)-2, 4-dioxo-1,2,3,4-tetrahydroquinazoline, 6-piperidino-2,4-dioxo-1,2,3,4-tetrahydroquinazoline, 6-morpholino-2,4-dioxo-1,2,3,4-tetrahydroquinazoline, 6-(4-methylpiperazinyl)-2,4-dioxo-1,2,3,4-tetrahydroquinazoline, 6-(4-chloromethylpiperazinyl)-2,4-dioxo-1,2,3,4-tetrahydroquinazoline, 6-(4-benzylpiperazinyl)-2,4-dioxo-1,2,3,4-tetrahydroquinazoline, 6-(4-(3-methoxybenzyl)piperazinyl) -2,4-dioxo-1,2,3,4-tetrahydroquinazoline, 6-(4-(phenylcarbonyl) piperazinyl)-2,4-dioxo-1,2,3,4-tetrahydroquinazoline, 6-(4-(3,4-dimethoxyphenylcarbonyl) piperazinyl)-2,4-dioxo-1,2,3,4-tetrahydroquinazoline, 6-(1-pyrrolylmethyl)-2,4-dioxo-1,2,3,4-tetrahydroquinazoline, 6-morpholinomethyl-2,4-dioxo-1,2,3,4-tetrahydroquinazoline, 7-(4-piperazinylmethyl)-2,4-dioxo-1,2,3,4-tetrahydroquinazoline, 6-(4-(3-phenylcarbonylpropyl) piperazinylcarbonyl)-2,4-dioxo-1,2, 3,4-tetrahydroguinazoline, 7-(4methylpiperazinylcarbonyl)-2,4-dioxo-1,2,3,4-tetrahydroquinazoline, 6-(4-benzylpiperidinocarbonyl)-2,4-dioxo-1,2,3,4-tetrahydroquinazoline, 6-acetoxy-2,4-dioxo-1,2,3,4-tetrahydroquinazoline, 6-propionyloxy-dioxo-1,2,3,4-tetrahydroquinazoline, 6-butylyloxy-2,4-dioxo-1,2,3,4-tetrahydroquinazoline, 6-i-butylyloxy-2,4-dioxo-1,2,3,4-tetrahydroquinazoline, 6-valeryloxy-2,4-dioxo-1,2,3,4-tetrahydroquinazoline, 6-pivaloyloxy-2,4-dioxo-1,2,3,4-tetrahydroquinazoline, 6-benzoyloxy-2,4-dioxo-1,2,3,4-tetrahydroquinazoline, 5,7-dimethyl-6propionyloxy-2,4-dioxo-1,2,3,4-tetrahydroquinazoline and 8-chloro-5,6-dimethoxy-2,4-dioxo-1,2,3,4-tetrahydroquinazoline.

The hexamethyldisilazane silylation agent may be used in a 1 to 10 fold molar amount, preferably from about 2 to 5 fold molar amount, relative to the amount of the tetrahydro quinazolines of formula (I).

The silylation reaction may be carried out in a solvent at from room temperature to the reflux temperature of the solvent. The reaction can be accelerated by carrying it out in the presence of a salt such as ammonium sulfate, ammonium chloride, guanidine hydrochloride and pyridine hydrochloride. In this case, the salt may be used in a 0.01 to 1 fold molar amount, preferably about 0.05 to 0.5 fold molar amount, relative to the amount of the tetrahydroquinazolines of formula (I).

The solvent may be any suitable solvent provided it does not inhibit the reaction. Examples thereof include aromatic hydrocarbons such as benzene, toluene and xylene; hydrocarbon halides such as dichloromethane and chloroform; ether solvents such as tetrahydrofuran and dioxane; and mixtures thereof. The solvent may be used in a 1 to 10 fold amount by weight, preferably about 1 to 3 fold amount by weight, relative to the amount of the tetrahydroquinazolines of formula (I).

The resultant 2,4-disilyl product may be used in the following step after isolation from the reaction mass, but is normally subjected to the following step as it is.

After silylation, the resultant product is reacted with the chloroalkanoate of formula (II) in the presence of the iodide of the alkaline metal, followed by desilylation. The substituent Z in the chloroalkanoate of formula (II) is a methylene group which is optionally substituted with an alkyl group and $R_6$ is an alkyl group or an aralkyl group. Examples of the alkyl group include a lower alkyl group as that exemplified above. Examples of the methylene group which is optionally substituted with an alkyl group include methylene and methylmethylene, preferably methylene. Examples of the aralkyl group include aralkyl group whose aromatic ring is optionally substituted with a nitro group, such as benzyl, 4-nitrobenzyl, phenylethyl, benzhydryl and trityl.

As the chloroalkanoate of formula (II), those wherein $R_6$ is a lower alkyl group are preferred. Examples include methyl chloroacetate, ethyl chloroacetate, propyl chloroacetate, t-butyl chloroacetate and ethyl 2-chloropropionate.

The chloroalkanoate of formula (II) may be used in a 1 to 5 fold molar amount relative to the amount of the tetrahydroquinazolines of formula (I).

The present invention is characterized by reacting the above-described chloroalkanoate (II) in the presence of the iodide of the alkaline metal. Examples of the iodide of the alkaline metal include potassium iodide, sodium iodide and lithium iodide. Among them, potassium iodide is preferably used.

The iodide of the alkali metal may be used in a 0.001 to 1 fold molar amount, preferably from about 0.1 to 1 fold molar amount, relative to the amount of the tetrahydroquinazolines of formula (I).

The reaction temperature with the chloroalkanoate (II) may be from about 0° C. to a boiling point of the solvent, preferably from about 80° C. to a boiling point of the solvent.

The desilylation can be carried out by, for example, adding water or an alcohol such as methanol, ethanol and i-propanol. These are normally used in a 2 to 30 fold molar amount, preferably from about 10 to 20 fold molar amount, relative to the amount of the tetrahydroquinazolines of formula (I).

Thus, 1-substituted tetrahydroquinazolines of formula (III), the objective product, are produced. When the objective product is deposited as a solid in the reaction mass, it can be removed from the reaction mass by, for example, filtration. When the objective product is dissolved in the reaction mass, it can be removed from the reaction mass by, for example, distilling off the solvent, adding water, extracting with an organic solvent and distilling off the organic solvent.

The 1-substituted tetrahydroquinazolines of formula (III) can also be removed in the form of a salt, for example, with an inorganic base, such as an alkali metal salt, alkaline earth metal salt and ammonium salt; salt with an organic base, such as an organic amine salt; addition salt with an inorganic acid, such as hydrochloride, hydrobromide, sulfate and phosphate; and addition salt with an organic acid, such as formate, acetate, trifluoroacetate, maleate, tartrate, methanesulfonate, benzenesulfonate and toluenesulfonate according to known processes.

The resultant 1-substituted tetrahydroquinazolines of formula (III) or salt thereof can also be further purified, for example, by recrystallization or various chromatographic treatments.

The 1-substituted tetrahydroquinazolines of formula (III) can be produced with high yield by reacting with the chloroalkanoate of formula (II) in the presence of the iodide of the alkaline metal.

The following Examples further illustrate the present invention in detail but are not to be construed to limit the scope thereof.

EXAMPLE 1

A mixture of 17.3 g of toluene, 10 g of 7-chloro-2,4-dioxo-1,2,3,4-tetrahydroquinazoline, 19.7 g of hexamethyldisilazane and 1 g of ammonium sulfate was refluxed for 2 hours with stirring, and then excess hexamethyldisilazane and toluene (26.3 g) were distilled off at 55° C. under a reduced pressure of 20 to 30 mmHg.

To this were added 8.45 g of potassium iodide and 27.6 g of ethyl chloroacetate and, after stirring continuously at 110 to 120° C. for 12 hours, 40 g of ethanol was added and the mixture was refluxed for 1 hour. After cooling to room temperature, the deposited crystals were filtered, washed with ethanol and water, and then dried to obtain 13.9 g of crystal.

The content of 2-(7-chloro-2,4-dioxo-1,2,3,4-tetrahydroquinazolin-1-yl)ethyl acetate in this was 100%. (yield 96.4%)

EXAMPLE 2

According to the same manner as that described in Example 1 except that the amount of hexamethyldisilazane was changed to 38.2 g, the time of reflux was changed to 5 hours, the amount of toluene distilled off was 40.8 g, the amount of potassium iodide was changed to 1.69 g and time of stirring was changed to 32 hours, the reaction was carried out to obtain 14.1 g of crystals.

The content of 2-(7-chloro-2,4-dioxo-1,2,3,4-tetrahydroquinazolin-1-yl)ethyl acetate in this crystal was 95.5%. (yield 93.7%).

Comparative Example 1

According to the same manner as that described in Example 1 except that potassium iodide was not used, the reaction was carried out to obtain 11.5 g of crystals.

The content of 2-(7-chloro-2,4-dioxo-1,2,3,4-tetrahydroquinazolin-1-yl)ethyl acetate in this crystal was 56.8%. (yield 45.7%)

What is claimed is:

1. A process for producing a 1-substituted tetrahydroquinazoline represented by formula (III):

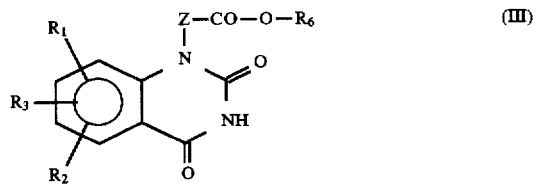

wherein

Z represents a methylene group;

$R_6$ represents an alkyl group or an aralkyl group;

$R_1$ and $R_2$ independently represent a hydrogen atom, a halogen atom, a nitro group, an azido group, an alkyl group, an alkenyl group, an aralkyl group, an alkoxy group, an alkoxycarbonyl group, a lower alkylcarbonyloxy group, an arylcarbonyl group, or an amino group represented by $XNR_4R_5$ in which X represents a direct bond, an alkylene group or a carbonyl group, and N, $R_4$ and $R_5$ may form together a five- or six-membered heterocyclic ring which optionally may have another nitrogen and/or oxygen atom or when X is a direct bond or an alkylene group, $R_4$ and $R_5$ independently may additionally represent an alkyl group or when X is a carbonyl group, $R_4$ and $R_5$ independently may additionally represent an acyloxy alkyl group; and $R_3$ represents a hydrogen atom, a halogen atom, a nitro group, an azido group, an alkyl group, an alkenyl group, an aralkyl group, an alkoxy group, or an alkoxycarbonyl group;

the process comprising the steps of reacting a tetrahydroquinazoline represented by the formula (I):

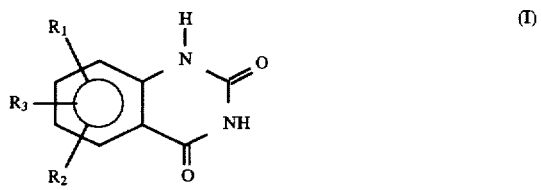
(I)

wherein $R_1$, $R_2$ and $R_3$ are as defined above with hexamethyldisilazane; and reacting the resultant product with a chloroalkanoate represented by the formula (II):

(II)

wherein Z and $R_6$ are as defined above in the presence of an iodide of an alkali metal, followed by desilylation.

2. The process according to claim 1, wherein the substituent $R_1$ of the tetraquinazoline (I) is a halogen atom and the substituent $R_2$ is a hydrogen atom.

3. The process according to claim 1, wherein the tetrahydroquinazolines (I) is 7-chloro-2,4-dioxo-1,2,3,4-tetrahydroquinazoline.

4. The process according to claim 1, wherein $R_6$ of the chloroalkanoate (II) is a lower alkyl group.

5. The process according to claim 1, wherein Z of the chloroalkanoate (II) is methylene or methylmethylene.

6. The process according to claim 1, wherein the chloroalkanoate (II) is ethyl chloroacetate.

7. The process according to claim 1, wherein the chloroalkanoate (II) is reacted with the resultant product of the tetrahydroquinazoline (I) and the hexamethyldisilazane in a 1- to 5-fold molar amount relative to the tetrahydroquinazoline (I).

8. The process according to claim 1, wherein the iodide of the alkaline metal is potassium iodide.

9. The process according to claim 1, wherein the process is carried out in at least one solvent selected from the group consisting of an aromatic hydrocarbon, a hydrocarbon halide and an ether solvent.

10. The process according to claim 1, wherein Z represents a methylene group which is substituted by an alkyl group.

11. The process according to claim 1, wherein $R_1$ and $R_2$ independently represent a hydrogen atom, a halogen atom, a nitro group, an azido group, an alkyl group which is substituted with one or more halogen atoms, an alkenyl group which is substituted with one or more halogen atoms, an aralkyl group which is substituted with one or more halogen atoms, an alkoxy group which is substituted with one or more halogen atoms, an alkoxycarbonyl group which is substituted with one or more halogen atoms, an alkoxy group, or an amino group represented by $XNR_4R_5$ in which X represents a direct bond, an alkylene group or a carbonyl group, and N, $R_4$ and $R_5$ may form together a five- or six-membered heterocyclic ring which contains another nitrogen atom which is substituted.

12. The process according to claim 1, wherein $R_3$ represents a hydrogen atom, a halogen atom, a nitro group, an azido group, an alkyl group which is substituted with one or more halogen atoms, an alkenyl group which is substituted with one or more halogen atoms, an aralkyl group which is substituted with one or more halogen atoms, an alkoxy group which is substituted with one or more halogen atoms, or an alkoxycarbonyl group which is substituted with one or more halogen atoms.

13. The process according to claim 11 wherein the substituent on said another nitrogen atom which is substituted is selected from the group consisting of an alkyl group, an aralkyl group, and a phenylcarbonyl group.

* * * * *